US006996242B2

(12) United States Patent
McLean et al.

(10) Patent No.: US 6,996,242 B2
(45) Date of Patent: Feb. 7, 2006

(54) INTEGRATED AND ACTIVE NOISE CONTROL INLET

(75) Inventors: Ian R. McLean, Chatham (CA); James K. Vanderveen, Blenheim (CA)

(73) Assignee: Siemens VDO Automotive Inc., Chatham (CA)

( * ) Notice: Subject to any disclaimer, the term of this patent is extended or adjusted under 35 U.S.C. 154(b) by 912 days.

(21) Appl. No.: 09/833,053

(22) Filed: Apr. 11, 2001

(65) Prior Publication Data

US 2002/0150259 A1 Oct. 17, 2002

Related U.S. Application Data

(60) Provisional application No. 60/209,754, filed on Jun. 6, 2000.

(51) Int. Cl.
*A61F 11/06* (2006.01)
*G10K 11/16* (2006.01)
*H03B 29/00* (2006.01)

(52) U.S. Cl. ..................... 381/71.5; 381/71.4; 381/71.7

(58) Field of Classification Search ................ 381/71.5, 381/71.4, 71.7, 86; 181/224
See application file for complete search history.

(56) References Cited

U.S. PATENT DOCUMENTS

| | | | |
|---|---|---|---|
| 3,936,606 | A | 2/1976 | Wanke |
| 4,410,065 | A | 10/1983 | Harvey |
| 4,665,549 | A | 5/1987 | Eriksson et al. |
| 4,876,722 | A | 10/1989 | Dekker et al. |
| 4,947,434 | A | 8/1990 | Ito |
| 5,106,397 | A | 4/1992 | Jaroszczyk et al. |
| 5,170,019 | A | 12/1992 | Lee |
| 5,229,556 | A | 7/1993 | Geddes |
| 5,319,165 | A | 6/1994 | Geddes |
| 5,336,856 | A | 8/1994 | Krider et al. |
| 5,426,703 | A | 6/1995 | Hamabe et al. |
| 5,426,705 | A | 6/1995 | Yokota et al. |
| 5,432,857 | A | 7/1995 | Geddes |
| 5,446,249 | A | 8/1995 | Goodman et al. |
| 5,446,790 | A | 8/1995 | Tanaka et al. |
| 5,457,749 | A | 10/1995 | Cain et al. |
| 5,466,899 | A | 11/1995 | Geisenberger |
| 5,513,266 | A | 4/1996 | Zuroski |
| 5,541,373 | A | 7/1996 | Cheng |
| 5,550,334 | A | 8/1996 | Langley |
| 5,587,563 | A | 12/1996 | Yazici et al. |
| 5,693,918 | A | 12/1997 | Bremigan et al. |
| 5,828,759 | A | 10/1998 | Everingham |
| 6,084,971 | A | 7/2000 | McLean |
| 2002/0126853 | A1 * | 9/2002 | Stuart ........................ 381/71.5 |

FOREIGN PATENT DOCUMENTS

| | | |
|---|---|---|
| DE | 19610292 | 9/1996 |
| EP | 0884471 | 12/1998 |
| EP | 0 884 471 A3 | 7/1999 |
| JP | 09126076 | 5/1997 |

OTHER PUBLICATIONS

European Search Report prepared for Application No. EP 01 20 1644 mailed Jul. 22, 2002.

* cited by examiner

*Primary Examiner*—Stella Woo

(57) ABSTRACT

A modular air induction assembly comprises an air induction body, an air filter operatively attached to the air induction body, and a speaker operatively attached to the air induction body. The modular air induction assembly is then installed into the air induction system of a vehicle during production. The air induction body may also comprise a first portion and a second portion that permits service of the assembly following initial vehicle installation.

18 Claims, 2 Drawing Sheets

INTEGRATED AND ACTIVE NOISE CONTROL INLET

This application claims priority to Provisional Patent Application Ser. No. 60/209,754 filed Jun. 6, 2000.

BACKGROUND OF THE INVENTION

This invention relates to an assembly for active control of automotive induction noise.

Manufacturers have employed active and passive methods to reduce engine noise within the passenger compartment of a motor vehicle. Such noise frequently emanates from the engine, travels through the air induction system and emanates out of the mouth of the air intake into the passenger compartment. Efforts have been made to reduce the amount of engine noise traveling through the air induction system. These efforts include the use of both passive devices such as expansion chambers and Helmholtz resonators and active devices involving anti-noise generators.

Active noise attenuation systems use a speaker to create a sound that attenuates engine noise. The sound created is out of phase with the engine noise and combines with the engine noise to result in its reduction. Generally, this sound is generated in proximity to the air induction system. In one such system, the speaker is placed in the mouth of air intake duct.

Typically, the speaker and other components of the active noise attenuation system are brought together with the components of the air induction system during vehicle assembly operations. However, separately assembling the noise attenuation system from the air induction system involves additional time-consuming steps. Such steps are undesirable during vehicle production.

SUMMARY OF THE INVENTION

In a disclosed embodiment of this invention, the components of the noise attenuation system and the air induction system are combined into a modular unit for quick assembly into a vehicle. The modular assembly includes an air induction body on which components of each system are attached. The air induction body may then be inserted into the remaining components of the air induction system, thereby avoiding additional assembly steps during vehicle production.

The modular assembly may comprise an air induction body with an attached air filter from the air induction system as well as a speaker from the noise attenuation system. An air inlet may be formed between the speaker and the air induction body to permit air flow into the air induction system. A channel may direct air from the air inlet to the air filter. This channel may be partially formed by a channel body, which may be a speaker housing or the air filter itself.

A control unit is in communication with the speaker and controls the speaker in a manner known in the art to attenuate engine noise. A sensor may supply data to the control unit for noise attenuation purposes. The air flow body may comprise a first portion and a second portion that are connected to each other to permit access to attached components for service.

With this assembly, a single modular unit is provided. The air flow body has elements of the air induction system and elements of the noise attenuation system all residing on the same body. This modular combination may then be quickly assembled into a vehicle during vehicle assembly operations. There is no longer a need to assemble the attached components at a point in production inconvenient to the automotive manufacturer. Moreover, following vehicle production and during the life of the vehicle, this combination may be removed and disassembled easily for quick service of the attached air induction and noise attenuation components. In this manner, the invention reduces the number of production steps and thereby simplifies and reduces the costs of vehicle production.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
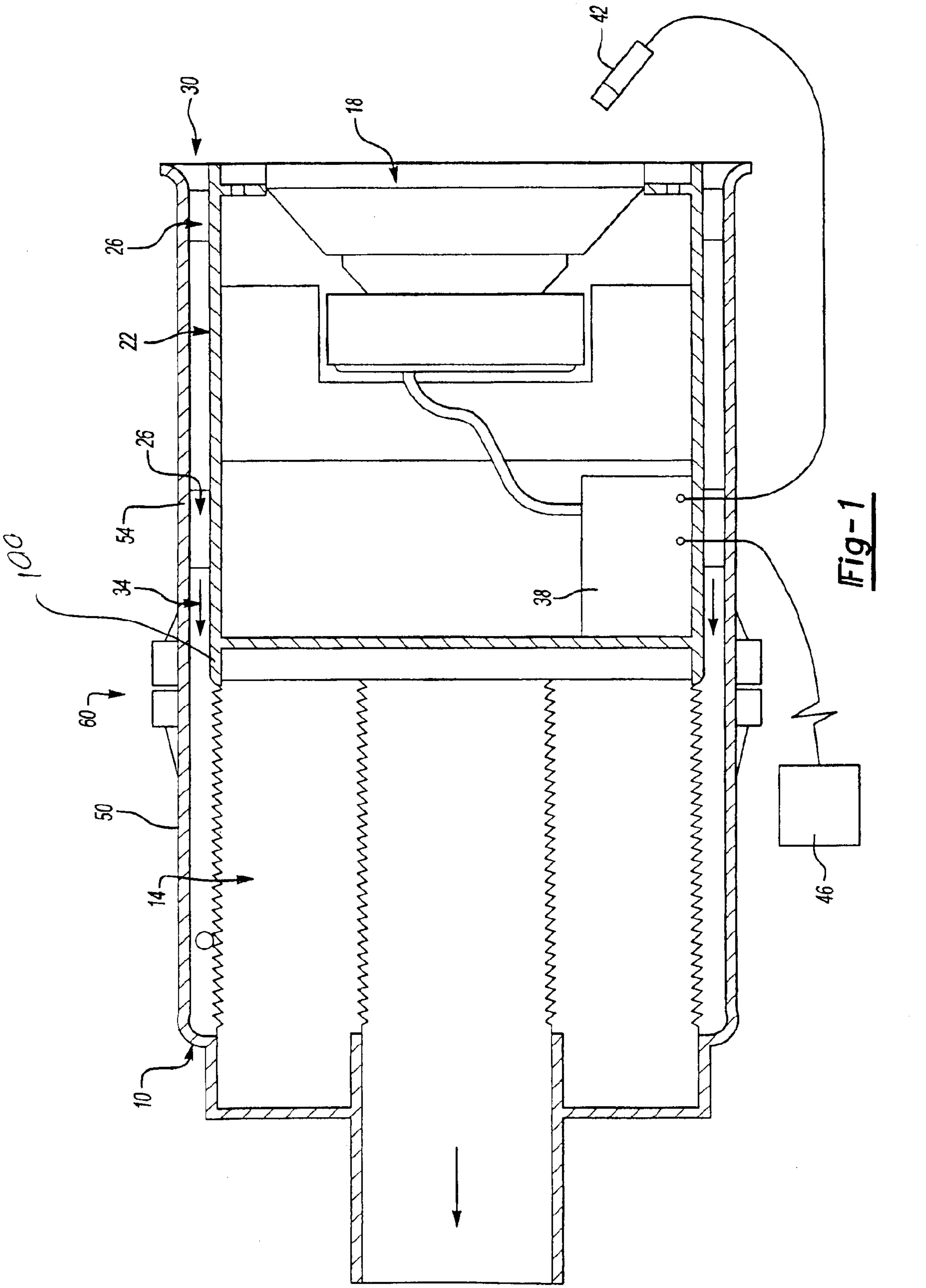
FIG. 1 shows an embodiment of the invention, including air flow body, speaker, and air filter.

FIG. 1 illustrates an embodiment of the invention, a modular air induction assembly, comprising air induction body 10, air filter 14, and speaker 18. As shown, air filter 14 and speaker 18 are operatively attached to air induction body 10. Here, in this particular embodiment, air filter 14 is a radial filter directly supported by air induction body 10. The combination of air induction body 10, air filter 14, and speaker 14 are modular to permit easy installation as part of a vehicle's air induction system.

Speaker 18 is of the type well known and used for noise attenuation systems and is supported by speaker housing 22. Speaker housing 22 may be mounted by struts 26 and attached to air induction body 10. At least one air inlet 30 may be formed between speaker 18 and air induction body 10 to permit air flow to air filter 14. Air passes air inlet 30 through channel 34 over guide surface 100, which is between air inlet 30 and air filter 14. Channel 34 may be at least partially formed by channel body, such as speaker housing 22 or air filter 14 as shown, or separately formed as part of the molding of air induction body 10.

Housed and supported by speaker housing 22 may be control unit 38, which is in communication with speaker 18 and controls speaker output as known in the art in a manner to attenuate engine noise. Control unit 18 may comprise a processor and audio amplifier as known. Sensors 42 and 46 may also be in communication with control unit 18. Sensor 42 is an error microphone while sensor 46 may be an engine speed sensor, such as a tachometer. Both sensors are commonly used and known in noise attenuation systems.

Figure 2:
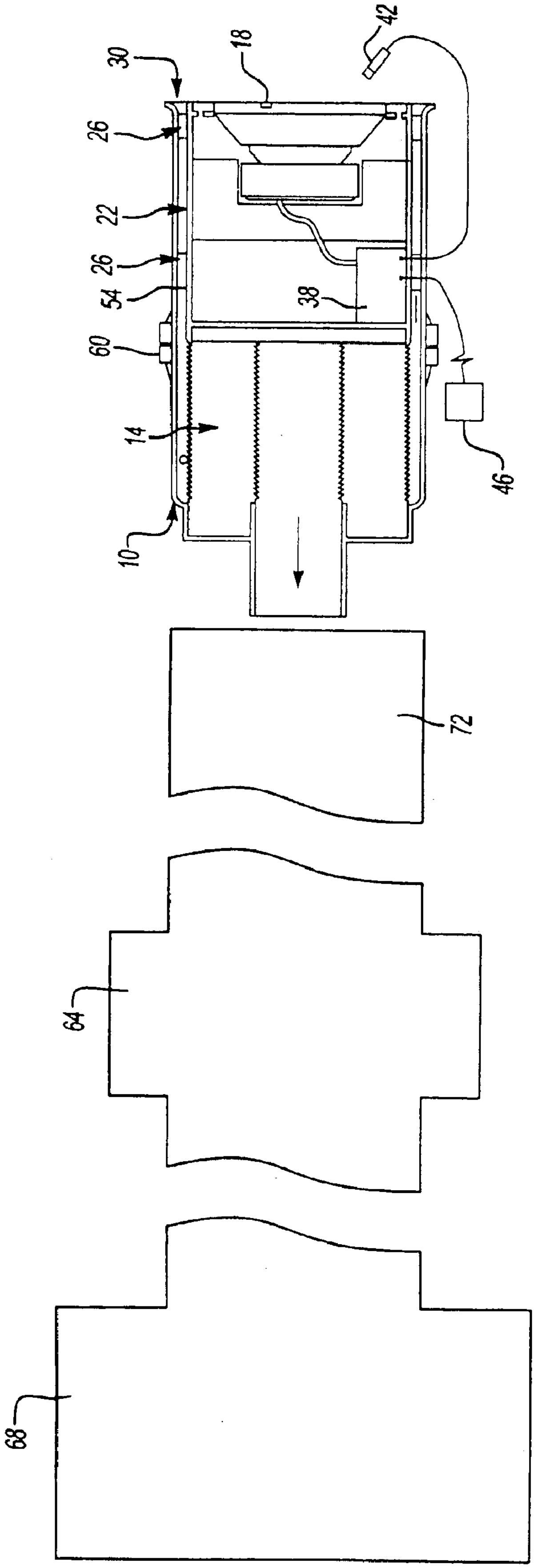
FIG. 2 shows the embodiment of FIG. 1 in relation to a vehicle throttle body and engine.

As a consequence of this modular assembly, air filter 14, speaker 18, and control unit 38 are easily installed as part of an air induction system during vehicle production. FIG. 2 illustrates the invention in its environment. Shown schematically are throttle body 64 and engine 68. In production sleeve 72 or other connection means known in the art receives the entire unit, including air induction body, speaker 18, control unit 38, and filter 14. The unit of FIG. 1 may be simply inserted into sleeve 72.

Additionally, air induction body 10 may comprise at least first portion 50 and second portion 54 and connection 60, which selectively permits disassembly of air induction body 10 into separate portions as known. Air filter 14, speaker 18, control unit 38 and other internal elements of air flow body

10 are then accessible. Accordingly, not only does the modular assembly permit its easy installation on the vehicle but allows for service of air filter 14, speaker 18, and control unit 38 following initial installation.

The aforementioned description is exemplary rather then limiting. Many modifications and variations of the present invention are possible in light of the above teachings. The preferred embodiments of this invention have been disclosed. However, one of ordinary skill in the art would recognize that certain modifications would come within the scope of this invention. Hence, within the scope of the appended claims, the invention may be practiced otherwise than as specifically described. For this reason the following claims should be studied to determine the true scope and content of this invention.

What is claimed is:

1. A modular air induction assembly comprising:

an air induction body;

an air filter operatively attached to said air induction body;

a speaker operatively attached to said air induction body;

at least one air inlet formed between said speaker and said air induction body to receive air; and at least one channel between said air inlet and said air filter to permit air flow to said air filter, wherein said air induction body comprises a first portion housing said air filter and a second portion housing said speaker, said first portion selectively engageable to said second portion.

2. The air induction system of claim 1 wherein said channel is at least partially formed by a channel body disposed in said air induction body.

3. The air induction system of claim 2 wherein said channel body is a speaker housing.

4. The air induction system of claim 2 wherein said channel body is said air filter.

5. The air induction system of claim 2 wherein said channel body comprises said air filter and said speaker housing, said channel body having a guide surface between said speaker housing and said air filter for directing airflow continuously from said speaker housing to said air filter.

6. The air induction system of claim 1 further including a control unit in communication with said speaker to attenuate engine noise, said control unit mounted to said channel body.

7. The air induction system of claim 6 further including a sensor in communication with said control unit.

8. The air induction system of claim 1 wherein said air induction body includes a connector for selectively engaging said first portion to said second portion.

9. A modular air induction assembly comprising:

an air induction body;

an air filter operatively attached to said air induction body;

a speaker operatively attached to said air induction body;

at least one air inlet formed between said speaker and said air induction body; and at least one channel between said air inlet and said air filter to permit air flow to said air filter, said air induction body selectively engageable to a throttle body by a connector.

10. The air induction system of claim 9 wherein said channel is at least partially formed by a channel body disposed in said air induction body.

11. The air induction system of claim 10 wherein said channel body is a speaker housing.

12. The air induction system of claim 10 wherein said channel body is said air filter.

13. The air induction system of claim 10 wherein said channel body comprises said air filter and said speaker housing.

14. The air induction system of claim 9 further including a control unit in communication with said speaker to attenuate engine noise.

15. The air induction system of claim 9 wherein said connection comprises a sleeve.

16. The air induction system of claim 9 wherein said air induction body comprises at least a first portion and a second portion, said first portion selectively engageable to said second portion.

17. A method of assembling an air induction system comprising:

providing an air flow body;

attaching a speaker to the air flow body;

attaching an air filter to the air flow body to form a modular combination; and then assembling the modular combination of air flow body, speaker, and air filter into a vehicle by inserting the air flow body into a sleeve sized to receive said air flow body.

18. The method of claim 17 further including the step of disassembling the modular combination for service.

* * * * *